United States Patent [19]

Shirasaka et al.

[11] Patent Number: 5,525,603
[45] Date of Patent: Jun. 11, 1996

[54] COMPOSITIONS, METHODS AND KITS FOR POTENTIATING ANTITUMOR EFFECT AND FOR TREATING TUMOR

[75] Inventors: Tetsuhiko Shirasaka, Kawagoe; Masakazu Fukushima, Otsu; Hideyuki Ohshimo, Hanno; Yuji Shimamoto, Otsu, all of Japan

[73] Assignee: Taiho Pharmaceutical Co., Ltd., Tokyo, Japan

[21] Appl. No.: 414,127

[22] Filed: Mar. 30, 1995

Related U.S. Application Data

[63] Continuation of Ser. No. 966,074, May 22, 1992, filed as PCT/JP92/00656, published as WO92/21345 Dec. 10, 1992, abandoned.

[30] Foreign Application Priority Data

May 27, 1991 [JP] Japan ................. 3-121247

[51] Int. Cl.⁶ .................. A61K 31/53; A61K 31/505; A61K 31/44
[52] U.S. Cl. .................. 514/241; 514/274; 514/348
[58] Field of Search .................. 514/241, 244, 514/348

[56] References Cited

U.S. PATENT DOCUMENTS

| | | |
|---|---|---|
| 5,116,600 | 5/1992 | Fujii et al. ............... 424/10 |
| 5,155,113 | 10/1992 | Fujii ............... 514/274 |

FOREIGN PATENT DOCUMENTS

| | | |
|---|---|---|
| 0443028A1 | 8/1991 | European Pat. Off. . |
| 55-111420 | 8/1980 | Japan . |
| 56-2913 | 1/1981 | Japan . |
| 56-46867 | 4/1981 | Japan . |
| 62-155215 | 7/1987 | Japan . |

OTHER PUBLICATIONS

Japanese J. Cancer Res. vol. 78, No. 7, 1987, pp. 748–755 "Inhibitory effects of pyrimidine, barbituric acid and pyridine derivatives on 5-fluorouracil degradation in rat liver extracts."
STN International, Karlsruhe, File Ca, Chemical Abstract "Oxonic acid for prevention of nausea and vomiting induced by 5-fluorouracils" (which corresponds to JP-A-5078249) published on Mar. 30, 1993.
Derwent Publication Ltd., corresponding to 56-46867. Apr. 28, 1981.

*Primary Examiner*—Jerome D. Goldberg
*Attorney, Agent, or Firm*—Nikaido, Marmelstein, Murray & Oram

[57] ABSTRACT

This invention provides a composition, method and kit for potentiating the antitumor effect of tegafur and reducing the side effects of tegafur, comprising a compound of the formula

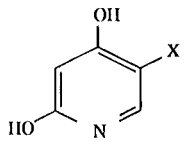

(I)

wherein X is a halogen atom or a cyano group and oxonic acid or a pharmaceutically acceptable salt thereof, and also provides a composition, method and kit for treating a tumor, comprising tegafur, a compound of the formula (I) and oxonic acid or a pharmaceutically acceptable salt thereof.

9 Claims, No Drawings

COMPOSITIONS, METHODS AND KITS FOR POTENTIATING ANTITUMOR EFFECT AND FOR TREATING TUMOR

This application is a continuation of application Ser. No. 07/966,074 filed Jan. 19, 1993, abandoned which is a 371 of PCT/JP92/00656 filed May 22, 1992.

TECHNICAL FIELD

The present invention relates to a composition, method and kit for potentiating the antitumor effect of tegafur, and a composition, method and kit for treating a tumor.

BACKGROUND ART

Japanese Examined Patent Publication (kokoku) No. 155215/1987 reports that a kind of pyridine compound can be used as a potentiator of antitumor effect of 5-fluorouracil (hereinafter referred to as "5-FU") and derivatives of 5-FU. The pyridine compound has the feature of sustaining the concentration of 5-FU in the living body. On the other hand, 5-FU is known to have the serious problem that the prolonged presence of 5-FU in the living body is likely to cause a disorder (inflammation) in the oral cavity, gastrointestinal tissue and the like as often experienced in continuous intravenous infusion of 5-FU alone.

International Publication WO 90/07334 reports that oxonic acid used in combination with 5-FU or 5-FU derivative can inhibit the occurrence of inflammation caused by 5-FU or 5-FU derivative. Yet oxonic acid in this case reduces the antitumor effect of 5-FU or 5-FU derivative. Thus oxonic acid is not satisfactory in terms of potentiation of antitumor effect and alleviation of adverse effects.

DISCLOSURE OF THE INVENTION

In the above-mentioned current situation, the present inventors conducted extensive research to increase the antitumor effect of tegafur and found that when tegafur is used in combination with a compound represented by the formula (I) below and oxonic acid or a pharmaceutically acceptable salt thereof, the antitumor effect of tegafur can be significantly increased while suppressing the side effects thereof such as inflammation and the like. The present invention has been accomplished based on this novel finding.

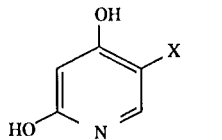
(I)

In the formula, X is a halogen atom or a cyano group.

The present invention provides an antitumor effect-potentiating composition for potentiating the antitumor effect of an antitumor composition containing a therapeutically effective amount of tegafur while suppressing the side effects of the antitumor composition, the antitumor effect-potentiating composition being characterized in that it contains a compound of the formula (I) in an amount effective for potentiating the antitumor effect, and oxonic acid or a pharmaceutically acceptable salt thereof in an amount effective for suppressing the side effects, as active ingredients, and a pharmaceutically acceptable carrier.

The present invention also provides an antitumor composition comprising a therapeutically effective amount of tegafur, an antitumor effect-potentiating effective amount of a compound of the formula (I) and a side effect-suppressing effective amount of oxonic acid or a pharmaceutically acceptable salt thereof, and a pharmaceutically acceptable carrier.

The antitumor effect-potentiating composition and the antitumor composition according to the invention are capable of potentiating the antitumor effect of tegafur, which is a known antitumor agent, without increasing the side effects or toxicity.

Tegafur for use in the invention is a medicament which is known to release 5-FU, i.e. an active precursor, on activation in the living body.

Accordingly the present invention further provides a method for treating a cancer susceptible to 5-fluorouracil therapy in a mammal, comprising administering to the mammal a therapeutically effective amount of tegafur, an antitumor effect-potentiating effective amount of a compound of the formula (I), and a side effect-suppressing effective amount of oxonic acid or a pharmaceutically acceptable salt thereof, and a method for potentiating the antitumor effect of tegafur and suppressing the side effects thereof in administering an antitumor composition containing a therapeutically effective amount of tegafur to a patient with a cancer susceptible to 5-fluorouracil therapy, the method being characterized by administering to the patient a compound of the formula (I) in an amount effective for potentiating the antitumor effect, and oxonic acid or a pharmaceutically acceptable salt thereof in an amount effective for suppressing the side effects.

In other words, the present invention particularly provides, in a method of treating a cancer susceptible to tegafur therapy in a patient in need of such treatment comprising administering to the patient a therapeutically effective amount of tegafur, the improvement comprising potentiating the antitumor effect by administering to the patient an antitumor effect-potentiating effective amount of the compound of the formula (I), while suppressing the side effects caused by administration of tegafur by administering to the patient oxonic acid or a pharmaceutically acceptable salt thereof in an amount effective for suppressing the side effects of tegafur.

The tegafur for use in the invention is a known compound and can be prepared by conventional processes as disclosed, e.g. in Japanese Examined Patent Publication No. 10510/1974.

The compounds of the formula (I) are all known and can be easily prepared by conventional processes. Examples of halogen atoms represented by X in the compound of the formula (I) are fluorine, chlorine, bromine and iodine atoms, etc. Preferred among the compounds of the formula (I) are 2,4-dihydroxy-5-chloropyridine, 2,4-dihydroxy-5-cyanopyridine, etc.

Oxonic acid per se is a known compound. Useful pharmaceutically acceptable salts thereof include acid addition salts and basic compound salts. Examples of useful acids capable of forming the acid addition salts are hydrochloric acid, sulfuric acid, phosphoric acid, hydrobromic acid and like inorganic acids, oxalic acid, succinic acid, maleic acid, fumaric acid, malic acid, tartaric acid, citric acid, malonic acid, methanesulfonic acid, benzoic acid and like organic acids. Examples of useful basic compounds capable of forming the pharmaceutically acceptable basic compound salts are sodium hydroxide, potassium hydroxide, calcium hydroxide, sodium carbonate, potassium hydrogencarbonate, etc. Usable as the oxonic acid are substances capable of producing oxonic acid in the living body such as ester derivatives of oxonic acid.

The antitumor effect-potentiating composition of the present invention is obtained by formulating the compound of the formula (I) and oxonic acid or a pharmaceutically acceptable salt thereof into a single preparation or into two respective separate preparations. The single preparation or two separate preparations can be administered either independently of or simultaneously with tegafur which is formulated in an optional dosage form. That is, the antitumor effect-potentiating composition of the present invention can be administered at any time before, after or simultaneously with the administration of tegafur. It is preferred to administer the antitumor effect-potentiating composition of the invention simultaneously with the administration of tegafur or within 4 hours before or within 4 hours after the administration of tegafur. The compound of the formula (I) and oxonic acid or a pharmaceutically acceptable salt thereof may be administered simultaneously or separately, and are in either case preferably administered simultaneously with the administration of tegafur or within 4 hours before or within 4 hours after the administration of tegafur. Generally the simultaneous administration of the compound of the formula (I) and oxonic acid or a pharmaceutically acceptable salt thereof is preferred even if they are provided in the form of separate preparations.

In the composition for potentiating the antitumor effect of tegafur comprising the compound of the formula (I) and oxonic acid or a pharmaceutically acceptable salt thereof as active ingredients according to the invention, it is preferable to use about 0.1 to about 10 moles, preferably about 0.5 to about 5 moles, of oxonic acid or a pharmaceutically acceptable salt thereof, per mole of the compound of the formula (I).

When the antitumor effect-potentiating composition of the invention is administered independently of or simultaneously with the administration of tegafur, particularly good results would be often obtained by administering the antitumor effect-potentiating composition of the invention in a manner such that about 0.1 to about 5 moles, preferably about 0.1 to about 1.5 moles, of the compound of the formula (I) and about 0.1 to about 5 moles, preferably about 0.2 to about 2 moles, of oxonic acid or a pharmaceutically acceptable salt thereof, are administered per mole of tegafur.

According to the present invention, an antitumor composition can be obtained by admixing tegafur with the antitumor effect-potentiating composition. In other words, the antitumor composition comprises three components, i.e., tegafur, a compound of the formula (I) and oxonic acid or a pharmaceutically acceptable salt thereof as active ingredients. The three active ingredients are admixed with a pharmaceutically acceptable carrier to provide a preparation in an optional unit dosage form which is then administered.

In the antitumor composition comprising tegafur, the compound of the formula (I) and oxonic acid or a pharmaceutically acceptable salt thereof as three active ingredients, it is suitable to use about 0.1 to about 5 moles, preferably about 0.1 to about 1.5 moles, of the compound of the formula (I), and about 0.1 to about 5 moles, preferably about 0.2 to about 2 moles, of oxonic acid or a pharmaceutically acceptable salt thereof, per mole of tegafur.

The proportions of the compound of the formula (I) and oxonic acid or a pharmaceutically acceptable salt thereof in this antitumor composition are not specifically limited and are suitably selected from the said range. A good result would often be obtained by using about 0.1 to about 10 moles, preferably about 0.5 to about 5 moles, of oxonic acid or a pharmaceutically acceptable salt thereof, per mole of the compound of the formula (I).

The antitumor effect-potentiating composition of the invention can be prepared in various dosage forms by adding a pharmaceutically acceptable carrier to the compound of the formula (I) and oxonic acid or a pharmaceutically acceptable salt thereof. In preparing the antitumor effect-potentiating composition of the invention, the compound of the formula (I) and oxonic acid or a pharmaceutically acceptable salt thereof may be provided in the form of a single preparation or two separate preparations.

The antitumor composition of the present invention is prepared, as described above, in the form of a single preparation containing both tegafur and the antitumor effect-potentiating composition, or in the form of two separate preparations wherein one comprises tegafur and the other comprises the antitumor effect-potentiating composition.

In either case, the foregoing pharmaceutical compositions are prepared in non-injection form by the conventional method using a suitable pharmaceutically acceptable carrier. Examples of useful carriers are those widely used in the manufacture of conventional pharmaceutical compositions, such as fillers, extenders, binders, disintegrators, surfactants, lubricants and like diluents and excipients.

The present invention also provides a kit comprising the compound of the formula (I) and oxonic acid or a pharmaceutically acceptable salt thereof. That is, the invention provides a kit for potentiating the antitumor effect of tegafur and suppressing the side effects of tegafur, comprising (i) the compound of the formula (I) in an amount effective for potentiating the antitumor effect of tegafur, and (ii) oxonic acid or a pharmaceutically acceptable salt thereof in an amount effective for suppressing the side effects of tegafur, the components (i) and (ii) being accommodated in separate containers.

Preferably the components (i) and (ii) are each provided in the form of a preparation containing a pharmaceutically acceptable carrier.

The present invention also provides a kit comprising tegafur and the antitumor effect-potentiating composition containing the compound of the formula (I) and oxonic acid or a pharmaceutically acceptable salt thereof either in a single preparation or in two separate preparations. Stated more specifically, the present invention provides a kit for treating a cancer in a mammal, comprising three components, i.e.

(i) a therapeutically effective amount of tegafur, (ii) the compound of the formula (I) in an amount effective for potentiating the antitumor effect of tegafur, and (iii) oxonic acid or a pharmaceutically acceptable salt thereof in an amount effective for suppressing the side effects of tegafur; and two or three containers holding the components (i), (ii) and (iii), the tegafur (i) being contained in a container different from the container(s) for the components (ii) and (iii). In the kit, the components (ii) and (iii) may be accommodated in separate containers, or a mixture of the components (ii) and (iii) may be held in a single container.

The components (i), (ii) and (iii) are preferably each in the form of a preparation containing a pharmaceutically acceptable carrier.

In the kits of the invention, the components may be administered simultaneously, or one or two components may be administered at any time before or after the administration of the other one component. Preferably the components may be administered simultaneously, or one or two components may be administered within 4 hours before or within 4 hours after the administration of the other one component. More preferably the components may be administered simultaneously, or one or two components may be administered within 2 hours before or within 2 hours after the administration of the other one component.

According to the kit of the invention, the antitumor effect of the antitumor composition containing tegafur as the active ingredient is significantly increased by the antitumor effect-potentiating composition comprising the compound of the formula (I) and oxonic acid or a pharmaceutically acceptable salt thereof in a single preparation or separate preparations, without increasing the level of toxicity such as gastrointestinal toxicity.

The present invention also provides the use of a combination of tegafur, a compound of the formula (I) and oxonic acid or a pharmaceutically acceptable salt thereof for preparing a composition for treating a cancer in a mammal with increased antitumor activity and suppressed side effects, and the use of a combination of the compound of the formula (I) and oxonic acid or a pharmaceutically acceptable salt thereof for preparing a composition for potentiating the antitumor effect of tegafur and suppressing the side effects of tegafur.

There is no particular restriction on the unit dosage form which can be adopted for the antitumor effect-potentiating composition or antitumor composition of the invention in the treatment of malignant tumors in mammals inclusive of human beings insofar as it is non-injection form. Thus, optional desired unit dosage form can be selected according to the purpose of treatment. Examples thereof are oral dosage forms such as tablets, coated tablets, pills, powders, granules, capsules, solutions, suspensions, emulsions, etc. and parenteral dosage forms such as suppositories, ointments, plasters, etc. These dosage forms can be manufactured by conventional pharmaceutical procedures known in this field.

As the carrier for shaping into the form of tablets, there can be employed various excipients such as lactose, sucrose, sodium chloride, glucose, urea, starch, calcium carbonate, kaolin, crystalline cellulose, silicic acid, etc.; binders such as simple syrup, glucose solution, starch solution, gelatin solution, carboxymethylcellulose, shellac, methylcellulose, potassium phosphate, polyvinylpyrrolidone, etc.; disintegrators such as dry starch, sodium alginate, agar powder, laminaran powder, sodium hydrogen carbonate, calcium carbonate, polyoxyethylene-sorbitan fatty acid esters, sodium lauryl sulfate, stearic acid monoglyceride, starch, lactose, etc.; antidisintegrators such as sucrose, stearic acid, cacao butter, hydrogenated oil, etc.; absorption promotors such as quaternary ammonium bases, sodium lauryl sulfate, etc.; humectants such as glycerol, starch, etc.; adsorbents such as starch, lactose, kaolin, bentonite, colloidal silicic acid, etc.; and lubricants such as purified talc, stearic acid salts, boric acid powder, polyethylene glycol, etc. Where necessary, the tablets may be in the form of coated tablets such as sugar-coated tablets, gelatin-coated tablets, enteric-coated tablets, film-coated tablets, or double or multi-layer tablets, etc.

The carrier for shaping into the form of pills includes, for example, various excipients such as glucose, lactose, starch, cacao butter, hardened vegetable oil, kaolin, talc, etc.; binders such as gum arabic powder, gum tragacanth powder, gelatin, etc.; and disintegrators such as laminaran, agar, etc.

The carrier for shaping into the form of suppositories includes, for example, polyethylene glycol, cacao butter, higher alcohols, esters of higher alcohols, gelatin, semi-synthetic glycerides, etc.

Capsules are manufactured by mixing the antitumor effect-potentiating composition, either alone or together with tegafur, with any of the carriers mentioned above and encapsulating the mixture in hard gelatin capsule, soft capsule or other capsules.

For manufacturing in the form of pastes, creams, and gels, there is employed a diluent such as, for example, white petrolatum, paraffin, glycerol, cellulose derivatives, polyethylene glycols, silicone, bentonite, etc.

When required, the above preparations may contain coloring agents, preservatives, perfumes, flavors, sweeteners, other medicament, etc.

The amounts of the compound of the formula (I) and oxonic acid or a pharmaceutically acceptable salt thereof, which are the active ingredients of the antitumor effect-potentiating composition of the present invention, and the amounts of tegafur, the compound of the formula (I) and oxonic acid or a pharmaceutically acceptable salt thereof, which are the active ingredients of the antitumor composition of the invention are dependent on the dosage form, route of administration, dosing schedule, etc. and can be appropriately chosen without specific limitation. Generally, however, the total amount of active ingredients in the dosage form may range from about 1 to about 70 percent by weight.

The route of administration of the antitumor effect-potentiating composition or antitumor composition of the present invention is not specifically limited insofar as it is non-injection route and may be, for example, intestinal, oral, rectal, stomatic, percutaneous or the like and can be selected according to the dosage form, the patient's age, sex and other factors, the severity of the symptom of the patient and so on. By way of example, tablets, pills, solutions, suspensions, emulsions, granules and capsules are orally administered. Suppositories are inserted into the rectum. Ointments are applied to the skin, the intraoral mucosa or the like.

In the present invention, the dosage of each active ingredient in each pharmaceutical composition can be selected according to the method of administration, the patient's age, sex and other factors, the degree of disease and so on. In the case of oral administration, the standard dosage for a human adult is usually about 0.1 to about 100 mg/kg/day, preferably about 1 to about 30 mg/kg/day, for tegafur, about 0.1 to about 100 mg/kg/day, preferably about 1 to about 50 mg/kg/day, for the compound of the formula (I) and about 0.1 to about 100 mg/kg/day, preferably about 1 to about 40 mg/kg/day, for oxonic acid or a pharmaceutically acceptable salt thereof. The compositions of the invention can each be administered daily in a single dose or in 2 to 4 divided doses. In the case of suppositories, for human adults, the equivalent of about 1 to 100 mg/kg of tegafur is administered into the rectum once or twice a day at an interval of 6 to 12 hours.

The malignant tumors which can be treated with the compositions of the invention may be any of the tumors susceptible to 5-FU which is the active precursor. Among them are cancers of the head and neck, stomach, colon, rectum, liver, gallbladder-bile duct, pancreas, lung, breast, urinary bladder, prostate, uterine cervix and so on.

EXAMPLES

The present invention will be described in more detail with reference to pharmacological tests, examples illustrating the preparation of antitumor effect-potentiating compositions of the invention and examples illustrating the preparation of antitumor compositions of the invention comprising the antitumor effect-potentiating composition and tegafur.

Pharmacological Test 1

(a) Preparation I of Test Suspensions

Tegafur (hereinafter referred to as "FT") and 2,4-dihydroxy-5-chloropyridine (hereinafter referred to as "ClDU") were suspended at concentrations of 2.0 mg/ml and 0.73 mg/ml, respectively, in a 1% solution of hydroxypropylmethylcellulose. The suspension was stirred by a stirrer at room temperature for about 20 minutes and subjected to ultrasonic treatment with ice-cooling for 5 minutes, giving a FT-ClDU mixed suspension (test suspension (1)). Two test suspensions (2) and (3) were prepared by adding a 1% solution of hydroxypropylmethylcellulose to test suspension (1) to give FT concentrations of 1.0 and 0.5 mg/ml, respectively.

(b) Preparation II of Test Suspensions

FT, ClDU and potassium oxonate were suspended at concentrations of 2.0 mg/ml, 0.73 mg/ml and 1.95 mg/ml, respectively, in a 1% solution of hydroxypropylmethylcellulose. The suspension was stirred by a stirrer at room temperature for about 20 minutes and subjected to ultrasonic treatment with ice-cooling for 5 minutes, giving a FT-ClDU-potassium oxonate mixed suspension (test suspension (4)). Test suspensions (5) and (6) were prepared by adding a 1% solution of hydroxypropylmethylcellulose to test suspension (4) to give FT concentrations of 1.0 and 0.5 mg/ml, respectively.

(c) Preparation III of Test Suspensions

Test suspensions (7) to (12) were prepared in the same manner as in Preparations I and II with the exception of using 1.46 mg/ml of ClDU.

(d) Preparation IV of Test Suspensions

"UFT" (product of Taiho Pharmaceutical Co., Ltd. containing uracil and FT in a molar ratio of 4:1) was suspended in a 1% solution of hydroxypropylmethylcellulose to obtain three suspensions each having FT concentrations of 1, 2 and 3 mg/ml, respectively. To the suspensions were added potassium oxonate to concentrations of 0.975 mg/ml, 1.95 mg/ml and 2.93 mg/ml, respectively. The suspensions were stirred by a stirrer at room temperature for about 20 minutes and subjected to ultrasonic treatment with ice-cooling, giving UFT-potassium oxonate mixed suspensions (test suspensions (13) to (15)).

(e) Preparation V of Test Suspensions

Test suspensions (16) to (21) were prepared in the same manner as in Preparations I and II with the exception of using 0.58 mg/ml of ClDU.

(f) Anti-cancer Experiment

Yoshida sarcoma cells were subcutaneously transplanted in an amount of $2 \times 10^4$ each into the back of 5-week-old Donryu-strain male rats. Then, 24 hours after the transplantation, each of the test suspensions (1) to (21) was orally administered to the rats at a dose of 1.0 ml per 100 g of body weight once a day. The administration was conducted for 7 consecutive days. A 1% solution of hydroxypropylmethylcellulose alone was orally administered to the cancer-bearing control rats.

The rats were sacrificed on day 8 after the transplantation of the tumor, and the tumor and gastrointestinal tissues were removed from the rats. The weight of tumor was measured and the tumor decrease ratio (%) was calculated from the following equation:

$$\text{Tumor decrease ratio} = [1 - (T/C)] \times 100$$

wherein T is the weight (g) of tumor of the group to which the test suspension was administered and C is the weight (g) of tumor of the control group.

Section samples were obtained from the digestive tract removed from the rats and observed under an optical microscope to check the sections for the degree of occurrence of inflammation of the digestive tract. The degree of occurrence of inflammation was evaluated according to the number of inflammatory sites and rated into 4 grades with (−) for no inflammation, (+) for a slight degree of inflammation, (++) for a medium degree of inflammation, and (+++) for a high degree of inflammation. The tissue samples were obtained by cutting open the removed digestive tract, washing them with a physiological saline and dipping them in a 10% neutral buffer formalin solution for fixation.

The body weight of the rats was measured with time to determine the body weight change (BWC) from the body weights measured before the transplantation of tumor and on day 8 after the transplantation. The therapeutic index (TI) was given by the following equation:

$$TI = BWC_{50}/ED_{50}$$

wherein $BWC_{50}$ is the concentration of FT at which increase in body weight becomes 50% compared with the control group and $ED_{50}$ is the concentration of FT at which increase in tumor weight becomes 50% compared with the control group.

The results are shown in Table 1 below. By the administration of UFT+potassium oxonate, increase in tumor weight did not become 50% or less compared with the control group, and therefore the $ED_{50}$ value was not obtained. In Table 1, "oxo" represents potassium oxonate.

TABLE 1

| Test suspension | Drug (Molar ratio) | Dose (*) (mg/kg) | Tumor decrease ratio (%) | Therapeutic index $BWC_{50}/ED_{50}$ | Digestive tract disorder |
|---|---|---|---|---|---|
| 3 | FT + ClDU | 5 | 16 | 1.28 | − |
| 2 | (1:0.5) | 10 | 73 | | + |
| 1 | | 20 | 100 | | ++ |
| 6 | FT + Oxo + ClDU | 5 | 36 | 2.50 | − |
| 5 | (1:1:0.5) | 10 | 65 | | − |
| 4 | | 20 | 99 | | − |
| 9 | FT + ClDU | 5 | 12 | 1.07 | − |
| 8 | (1:1) | 10 | 90 | | + |
| 7 | | 20 | 100 | | +++ |
| 12 | FT + Oxo + ClDU | 5 | 30 | 1.84 | − |
| 11 | (1:1:1) | 10 | 86 | | − |
| 10 | | 20 | 99 | | − |

TABLE 1-continued

| Test suspension | Drug (Molar ratio) | Dose (*) (mg/kg) | Tumor decrease ratio (%) | Therapeutic index $BWC_{50}/ED_{50}$ | Digestive tract disorder |
|---|---|---|---|---|---|
| 13 | UFT + Oxo | 10 | 0 | | |
| 14 | (1:1) | 20 | 42 | | |
| 15 | | 30 | 24 | | |
| 18 | FT + CIDU | 5 | 28 | 0.76 | |
| 17 | (1:0.4) | 10 | 20 | | + |
| 16 | | 20 | 100 | | ++ |
| 21 | FT + Oxo + CIDU | 5 | 0 | >2.35 | |
| 20 | (1:1:0.4) | 10 | 72 | | |
| 19 | | 20 | 99 | | |

(*) Amount of FT

Pharmacological Test 2

(a) Preparation I of Test Suspension

FT and 2,4-dihydroxy-5-cyanopyridine (hereinafter referred to as "CNDU") were suspended at concentrations of 3.0 mg/ml and 1.02 mg/ml, respectively, in a 1% solution of hydroxypropylmethylcellulose. The suspension was stirred by a stirrer at room temperature for about 20 minutes and subjected to ultrasonic treatment with ice-cooling for 5 minutes, giving a FT-CNDU mixed suspension (test suspension (1)).

(b) Preparation II of Test Suspension

FT, CNDU and potassium oxonate were suspended at concentrations of 3.0 mg/ml, 1.02 mg/ml and 2.93 mg/ml, respectively, in a 1% solution of hydroxypropylmethylcellulose. The suspension was stirred by a stirrer at room temperature for about 20 minutes and subjected to ultrasonic treatment with ice-cooling for 5 minutes, giving a FT-CNDU-potassium oxonate mixed suspension (test suspension (2)).

(c) Anti-cancer Experiment

Sarcoma S-180 cells were subcutaneously transplanted in an amount of $1 \times 10^7$ each into the back of 4-week-old ICR strain male mice. Then, 24 hours after the transplantation, each of the test suspensions (1) and (2) was orally administered to the mice at a dose of 1.0 ml per 100 g of body weight once a day. The administration was conducted for 7 consecutive days. A 1% solution of hydroxypropylmethylcellulose alone was orally administered to the cancer-bearing control mice.

The mice were sacrificed on day 10 after the transplantation of the tumor, and the tumor was removed from the mice to measure the weight of tumor. The tumor decrease ratio (%) was calculated from the following equation.

Tumor decrease ratio=$[1-(T/C)] \times 100$ wherein T is the weight (g) of tumor of the group to which the test suspension was administered and C is the weight (g) of tumor of the control group.

The body weight of the mice was measured with time, and the body weight gain was determined from the body weights of mice measured before the trasplantation of tumor and 10 days after the transplantation to obtain a percent body weight change (%) according to the following equation:

Percent body weight change=$(TBI/CBI) \times 100$ wherein TBI is the body weight gain (g) of the group to which the test suspension was administered and CBI is the body weight gain (g) of the control group.

Table 2 below shows the results. In Table 2 "oxo" represents potassium oxonate.

TABLE 2

| Test suspension | Drug (Molar ratio) | Dose(*) (mg/kg) | Tumor decrease ratio (%) | Percent body weight change (%) |
|---|---|---|---|---|
| 1 | FT + CNDU (1:0.5) | 30 | 58 | 56 |
| 2 | FT + Oxo + CNDU (1:1:0.5) | 30 | 62 | 89 |

(*) Amount of FT

Pharmacological Test 3

(a) Preparation I of Test Drug

FT and CIDU were used in amounts of 6 mg and 1.74 mg, respectively, per kg of body weight of a beagle dog. These two components were encapsulated in gelatin capsules for animals (No. 13, ⅛ ounce), and mixed with thorough shaking, giving a FT-CIDU mixture (test drug (1)).

(b) Preparation II of Test Drug

FT, CIDU and potassium oxonate were used in amounts of 6 mg, 1.74 mg and 5.88 mg, respectively, per kg of body weight of a beagle. These components were encapsulated in gelatin capsules for animals (No. 13, ⅛ ounce), and mixed with thorough shaking, giving a FT-CIDU-potassium oxonate mixture (test drug (2)).

(c) Preparation III of Test Drug

FT and uracil were used in amounts of 20 mg and 44.8 mg, respectively, per kg of body weight of a beagle dog. The two components were encapsulated in gelatin capsules for animals (No. 13, ⅛ ounce), and mixed with thorough shaking, giving a FT-uracil mixture (test drug (3)).

(d) Pharmacological Test

Each of test drugs (1) to (3) was forcibly administered to male beagle dogs weighing 9 to 10 kg through oral route. Test drugs (1) and (2) were administered once a day for 5 consecutive days. The test drug (3) was administered once a day for 4 consecutive days.

During the above oral administration period, the dogs were observed every day for occurrence of vomiting and diarrhea (digestive tract disorder). The degree of diarrhea was rated (−) when the stool was normal to loose stool, and rated (+) when the stool was mucous stool or liquid stool. Observation was continued until the day following the day of final administration to count the number of dogs with which vomiting or diarrhea (+) was observed at least once during the period of observation.

Table 3 shows the results. In Table 3, "oxo" denotes potassium oxonate.

TABLE 3

| Test drug | Drug (Molar ratio) | Dose (*) (mg/kg) | Number of administration | Number of animals | Occurrence of vomiting | Occurrence of diarrhea |
|---|---|---|---|---|---|---|
| 1 | FT + ClDU (1:0.4) | 6 | 5 | 11 | 7/11 | 10/11 |
| 2 | FT + Oxo + ClDU (1:1:0.4) | 6 | 5 | 11 | 1/11 | 1/11 |
| 3 | FT + Uracil (1:4) | 20 | 4 | 6 | 6/6 | 0/6 |

(*) Amount of FT

Formulation Example 1: Tablet

| ClDU | 41 mg |
|---|---|
| Potassium oxonate | 60 mg |
| Starch | 112 mg |
| Magnesium stearate | 17 mg |
| Lactose | 45 mg |
| Total | 275 mg |

Using the conventional procedure, tablets each weighing 275 mg were prepared according to the above formula.

Formulation Example 2: Tablet

| Tegafur | 30 mg |
|---|---|
| ClDU | 20 mg |
| Potassium oxonate | 30 mg |
| Starch | 110 mg |
| Magnesium stearate | 17 mg |
| Lactose | 43 mg |
| Total | 250 mg |

Using the conventional procedure, tablets each weighing 250 mg were prepared according to the above formula.

Formulation Example 3: Tablet

| CNDU | 16 mg |
|---|---|
| Potassium oxonate | 50 mg |
| Lactose | 45 mg |
| Crystalline cellulose | 20 mg |
| Magnesium stearate | 5 mg |
| Talc | 4 mg |
| Methylcellulose | 10 mg |
| Total | 150 mg |

Using the conventional procedure, tablets each weighing 150 mg were prepared according to the above formula.

Formulation Example 4: Tablet

| Tegafur | 40 mg |
|---|---|
| CNDU | 10 mg |
| Potassium oxonate | 38 mg |
| Lactose | 54 mg |
| Crystalline cellulose | 20 mg |
| Magnesium stearate | 5 mg |
| Talc | 3 mg |
| Methylcellulose | 10 mg |
| Total | 180 mg |

Using the conventional procedure, tablets each weighing 180 mg were prepared according to the above formula.

Formulation Example 5: Granule

| ClDU | 50 mg |
|---|---|
| Potassium oxonate | 150 mg |
| Lactose | 340 mg |
| Corn starch | 450 mg |
| Hydroxypropylmethylcellulose | 10 mg |
| Total | 1000 mg |

Using the conventional procedure, granules were prepared according to the above formula.

Formulation Example 6: Granule

| Tegafur | 200 mg |
|---|---|
| ClDU | 50 mg |
| Potassium oxonate | 150 mg |
| Lactose | 340 mg |
| Corn starch | 450 mg |
| Hydroxypropylmethylcellulose | 10 mg |
| Total | 1200 mg |

Using the conventional procedure, granules were prepared according to the above formula.

Formulation Example 7: Suppository

| Tegafur | 300 mg |
|---|---|
| ClDU | 300 mg |
| Potassium oxonate | 400 mg |
| Witepsol W-35 | 900 mg |
| Total | 1900 mg |

Using the conventional procedure, suppositories were prepared according to the above formula.

We claim:

1. An antitumor effect-potentiating composition for potentiating the antitumor effect of an antitumor composition containing a therapeutically effective amount of tegafur while suppressing the side effects of the antitumor composition, the antitumor effect-potentiating composition comprising 2,4-dihydroxy-5-chloropyridine in an amount effective for potentiating the antitumor effect, and oxonic acid or a pharmaceutically acceptable salt thereof in an amount effective for suppressing the side effects, as active ingredients, and a pharmaceutically acceptable carrier, wherein (B) 2,4-dihydroxy-5-chloropyridine and (C) oxonic acid or a pharmaceutically acceptable salt thereof are used in a molar ratio of (B):(C)=0.4:1.

2. The antitumor effect-potentiating composition of claim 1, wherein said pharmaceutically acceptable salt is potassium oxonate.

3. An antitumor composition comprising a therapeutically effective amount of tegafur, an antitumor effect-potentiating effective amount of 2,4-dihydroxy-5-chloropyridine, a side effect-suppressing effective amount of oxonic acid or a pharmaceutically acceptable salt thereof, and a pharmaceutically acceptable carrier, wherein (A) tegafur, (B) 2,4-dihydroxy-5-chloropyridine and (C) oxonic acid or a pharmaceutically acceptable salt thereof are used in a molar ratio of (A):(B):(C)=1:0.4:1.

4. The antitumor composition of claim 3, wherein said pharmaceutically acceptable salt is potassium oxonate.

5. A method for treating a cancer in a mammal wherein the cancer is susceptible to 5-fluorouracil therapy, the method comprising administering to the mammal a therapeutically effective amount of tegafur, an antitumor effect-potentiating effective amount of 2,4-dihydroxy-5-chloropyridine, and a side effect-suppressing effective amount of oxonic acid or a pharmaceutically acceptable salt thereof, wherein (A) tegafur, (B) 2,4-dihydroxy-5-chloropyridine and (C) oxonic acid or a pharmaceutically acceptable salt thereof are used in a molar ratio of (A):(B):(C)=1:0.4:1.

6. A method for potentiating the antitumor effect of tegafur and suppressing the side effects thereof in administering an antitumor composition containing a therapeutically effective amount of tegafur to a patient with a cancer susceptible to 5-fluorouracil therapy, the method comprising administering to the patient 2,4-dihydroxy-5-chloropyridine in an amount effective for potentiating the antitumor effect, and oxonic acid or a pharmaceutically acceptable salt thereof in an amount effective for suppressing the side effects, wherein (B) 2,4-dihydroxy-5-chloropyridine and (C) oxonic acid or a pharmaceutically acceptable salt thereof are used in a molar ratio of (B):(C)=0.4:1.

7. A method according to claim 6 wherein an antitumor effect-potentiating effective amount of 2,4-dihydroxy-5-chloropyridine and a side effect-suppressing effective amount of oxonic acid or a pharmaceutically acceptable salt thereof are administered to the patient within 4 hours before or within 4 hours after the administration of the antitumor composition.

8. A method according to claim 6 wherein an antitumor effect-potentiating effective amount of 2,4-dihydroxy-5-chloropyridine and a side effect-suppressing effective amount of oxonic acid or a pharmaceutically acceptable salt thereof are administered to the patient simultaneously with the administration of the antitumor composition.

9. The method of claim 6, wherein said pharmaceutically acceptable salt is potassium oxonate.

* * * * *